United States Patent [19]

Levitt

[11] 4,379,769
[45] Apr. 12, 1983

[54] PROCESS FOR PREPARING ARYLSULFONYL ISOCYANATES BY PHOSGENATION OF ARYLSULFONAMIDES

[75] Inventor: George Levitt, Wilmington, Del.

[73] Assignee: E. I. Du Pont de Nemours and Company, Wilmington, Del.

[21] Appl. No.: 192,707

[22] Filed: Oct. 1, 1980

Related U.S. Application Data

[63] Continuation-in-part of Ser. No. 45,244, Jun. 4, 1979, abandoned.

[51] Int. Cl.³ .......................................... C07C 143/79
[52] U.S. Cl. .................................................. 260/545 R
[58] Field of Search ........................................ 260/545

[56] References Cited

U.S. PATENT DOCUMENTS 2,362,648 11/1944 Lichty et al. .
3,371,114 2/1968 Sayigh et al. ........................ 260/545
3,379,758 4/1968 Ulrich ................................. 260/545
3,484,466 12/1969 Sayigh et al. ..................... 260/397.7
3,689,549 9/1972 Williams ......................... 260/545 R

FOREIGN PATENT DOCUMENTS 2152971 4/1973 Fed. Rep. of Germany .
2450083 4/1976 Fed. Rep. of Germany ...... 260/545
692360 6/1953 United Kingdom .

OTHER PUBLICATIONS

Ulrich et al., *J. Org. Chem.*, 31, 2658 (1966).
Kurzer, *Chem. Rev.*, 50, 1–46 (1951).
Fiesen et al., Reagents for Organic Synthesis, 1, 856–8,1200–2 (1967), 2 106,328–9 (1969).

*Primary Examiner*—Robert Gerstl

[57] ABSTRACT

An improved process for preparing arylsulfonyl isocyanates by phosgenation of arylsulfonamides in the presence of a catalytic quantity of a hydrocarbyl isocyanate and a catalytic quantity of a tertiary amine base. The sulfonyl isocyanates are useful intermediates.

14 Claims, 1 Drawing Figure

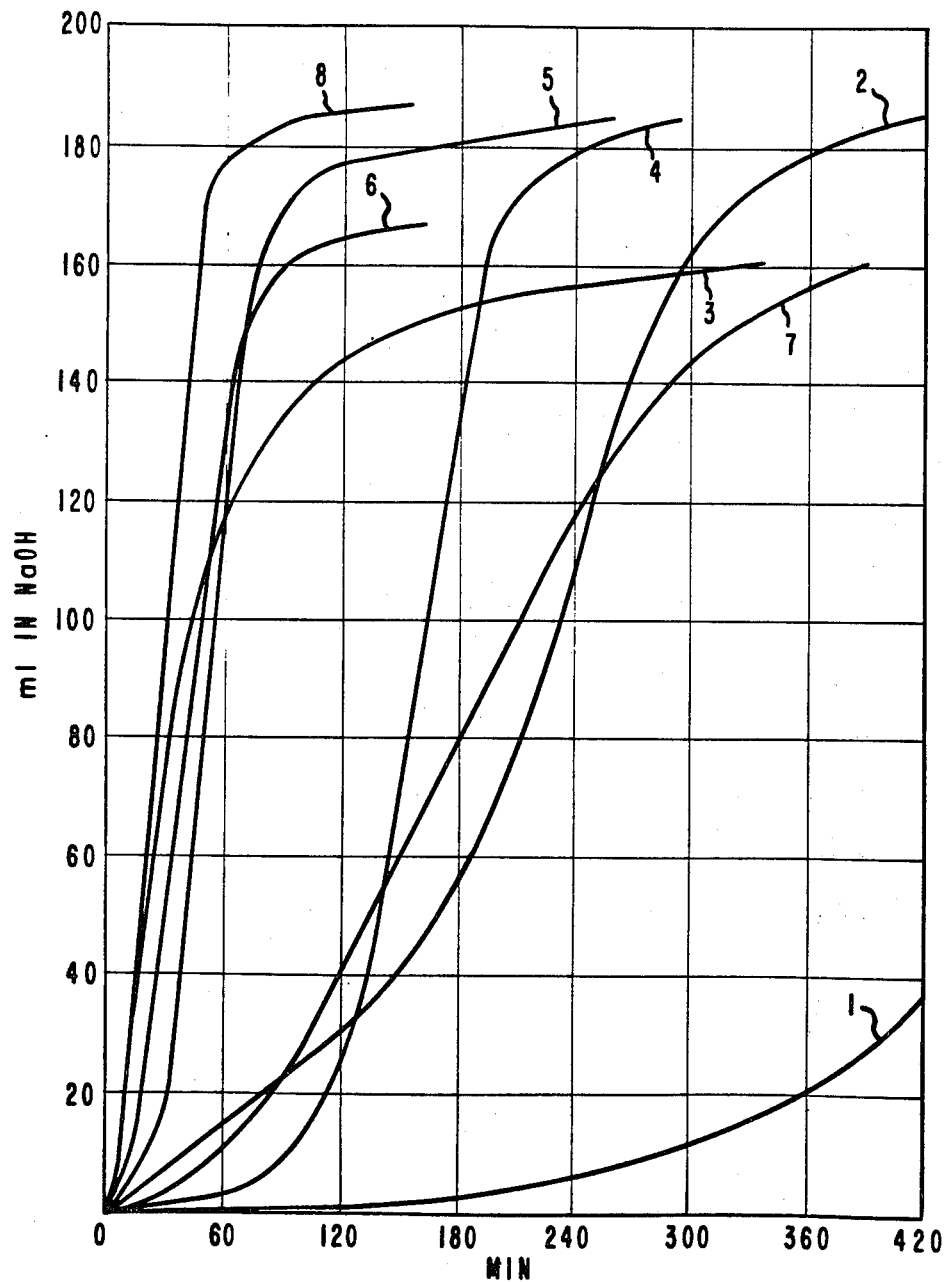

PROCESS FOR PREPARING ARYLSULFONYL ISOCYANATES BY PHOSGENATION OF ARYLSULFONAMIDES

RELATED APPLICATIONS

This application is a continuation-in-part of copending application U.S. Ser. No. 045,244, filed June 4, 1979, now abandoned.

BACKGROUND OF THE INVENTION

Arylsulfonyl isocyanates are known to be useful intermediates in the production of a variety of compounds. They can be used for preparing hypoglycemic drugs as described in Logemann et al., *Chem. Abs.* 53, 18052g (1959) and Wojciechowski, *J. Acta. Polon. Pharm.*, 19, 121–125 (1962), as well as for preparing novel herbicides such as those described in U.S. Pat. Nos. 4,127,405 and 4,120,691.

It is known in the art to prepare arylsulfonyl isocyanates by the reaction of the corresponding arylsulfonamides with phosgene in an inert solvent. As described in British Pat. No. 692,360, this reaction requires a temperature in the range of 160° to 250° C. as well as a large excess of phosgene.

U.S. Pat. Nos. 3,371,114 and 3,484,466 teach the preparation of arylsulfonyl isocyanates by phosgenation of arylsulfonamides in the presence of a catalytic quantity of a hydrocarbyl isocyanate. This reaction is carried out in an inert solvent at a temperature between 60° and 200° C.

The phosgenation of N-arylsulfonyl-N'-alkylureas at temperatures of from 0° to 175° C. to prepare arylsulfonyl isocyanates is described in U.S. Pat. No. 3,379,758.

In U.S. Pat. No. 3,689,549, the phosgenation of a sulfonamide in a sulfolane solvent is taught to produce a sulfonyl isocyanate of increased purity.

German Pat. No. 2,152,971 teaches a process for preparing sulfonyl isocyanates by reacting sulfonamides with phosgene in an inert solvent, in which the reaction is carried out in the presence of mono- and/or poly-primary amines in such an amount that there is less than 0.1 equivalent of primary amino groups per equivalent of sulfonamide groups.

U.S. Pat. No. 2,362,648 discloses a method for preparing isocyanates by reacting an amine with phosgene in the presence of a tertiary amine catalyst.

Although the prior art describes several processes for preparing arylsulfonyl isocyanates, there exists a need for an even more efficient and economical process for preparing these useful compounds.

SUMMARY OF THE INVENTION

According to this invention, there is provided an improved process for preparing arylsulfonyl isocyanates by the phosgenation of an arylsulfonamide in the presence of a catalytic quantity of a hydrocarbyl isocyanate and a catalytic quantity of a tertiary amine base.

This new and improved process results in the formation of the desired arylsulfonyl isocyanates in improved yields and purity and can be run at lower temperatures and in a shorter reaction time than prior art processes. Thus, considerable savings in materials and energy may be effected.

DETAILED DESCRIPTION OF THE INVENTION

The preparation of the arylsulfonamides used in the process claimed herein is known in the art. The preparation of arylsulfonamides from ammonium hydroxide and arylsulfonyl chloride is widely reported in the literature, e.g., Crossley et al., *J. Am. Chem. Soc.* 60, 2223 (1938). Certain arylsulfonyl chlorides are best prepared by chlorosulfonation of a substituted benzene in carbon tetrachloride according to the teaching of H. T. Clarke et al., *Org. Synth. Coll.* Vol. 1, 2nd Ed., 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25, 1824 (1960).

The process of this invention may be illustrated by the following formula:

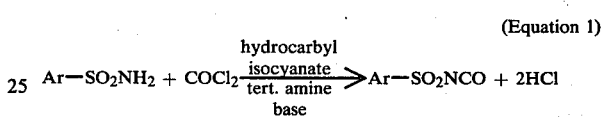

(Equation 1)

U.S. Pat. No. 3,371,114, herein incorporated by reference, teaches the use of a catalytic quantity of a hydrocarbyl isocyanate in a phosgenation reaction of this type. The arylsulfonamides employed as starting materials in this process are as described in that patent. Basically, the arene moiety of the arenesulfonamide can be the residue of any monocyclic or polycyclic aromatic hydrocarbon. Examples of suitable arene moieties are phenyl, naphthyl, biphenylyl, phenanthryl, and anthracenyl, all of which ca be substituted at any position by groups unreactive with phosgene.

A preferred embodiment of this invention, due to increased reaction rates, is the phosgenation of a 2-substituted aryl 1-sulfonamide, the 2-substituent being any group unreactive with phosgene, as previously described. More preferred, due to increased reaction rates and/or the high herbicidal activity of compounds made from the product isocyanates are those processes of this invention where, independently, (1) the arylsulfonamide is substituted at the 2-position with an electron-withdrawing group and (2) the arylsulfonamide is a benzenesulfonamide. Electron-withdrawing substituents include, but are not limited to Cl, F, Br, $NO_2$, $CF_3$, $(C_1-C_4 \text{ alkyl})SO_2$— and $(C_1-C_2 \text{alkyl})_2NSO_2$—.

Most preferred, for the same reasons mentioned above, is the process of this invention wherein an arylsulfonamide of the formula

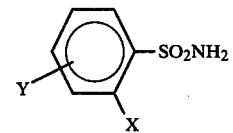

where

X is Cl, F, Br, $CF_3$, $(C_1-C_4\text{alkyl})SO_2$—, $(C_1-C_2 \text{ alkyl})_2NSO_2$, $NO_2$, $CH_3$ or $OCH_3$; and Y is H, Cl, F, Br, $CH_3$ or $OCH_3$;

is phosgenated. Also, most preferred is the phosgenation of the specific compounds o-chlorobenzenesulfonamide, o-nitrobenzenesulfonamide and 2,5-dichlorobenzenesulfonamide according to the process of this invention.

The hydrocarbyl isocyanates which are useful in the process claimed herein are also described in the above-cited patent, U.S. Pat. No. 3,371,114. As disclosed therein, the only limitation on the nature of the hydrocarbyl moiety is that it should be free from substituents which are reactive with phosgene. Preferred in this invention for reasons of efficiency and economy are the $C_4$–$C_{10}$ alkyl isocyanates and the $C_5$–$C_8$ cycloalkyl isocyanates. For the purposes of this invention, a catalytic quantity of hydrocarbyl isocyanate will generally consist of an amount equal to about 0.2 to 1.0 mole of hydrocarbyl isocyante per mole of arylsulfonamide.

The improvement over the prior art found in the claimed process lies in carrying out the phosgenation reaction in the presence of a catalytic quantity of a tertiary amine base. Any tertiary amine base free of substituents reactive with phosgene may be used. Classes of tertiary amines which could be used include, but are not limited to, aliphatic, cycloaliphatic, aliphaticaromatic, heterocyclic and aliphaticheterocyclic amines. Preferred for reasons of availability are those tertiary amines containing from three to ten carbon atoms and one to two nitrogen atoms. Examples of such bases are pyridine, triethylamine 1,4-diazabicyclo[2,2,2]octane, 4-dimethylaminopyridine, N,N-dimethylaniline, trimethylamine, N,N-diethylaniline, N-methylpiperidine, and N,N'-dimethylpiperazine. Preferred for reasons of efficiency and economy are 1,4-diazabicyclo[2,2,2]octane and triethylamine.

The tertiary amine base must be present in a catalytic quantity. This will generally be in the range of about 0.2 to 5.0 grams of base per mole of arylsulfonamide.

The process of this invention is generally carried out within a temperature range of about 100°–175° C. although temperature is not critical. Pressure is also not critical, and atmospheric pressure is typically used.

The time required for the reaction to go to substantial completion may be readily monitored by techniques familiar to one skilled in the art, e.g., titration of the effluent hydrogen chloride gas or infrared analysis of the reaction mixture. Typically, the reaction time will be in the range of about 1 to 24 hours.

A suspension of the appropriate arylsulfonamide in an inert solvent, a catalytic quantity of hydrocarbyl isocyanate and a catalytic quantity of a tertiary amine base are heated, with stirring, to reflux. The solvent can be any inert solvent with a boiling point within the range of about 100°–200° C.; examples of suitable solvents are xylene, chlorobenzene, mesitylene, toluene, pentachloroethane and octene. Phosgene is then introduced under a refrigerated reflux condenser at such a rate that the temperature of the reaction mass is maintained at about 5° to 8° C. below the boiling point of the solvent. Following the phosgene addition, the reaction mixture is heated to drive off the small amount of excess phosgene, and is then cooled and filtered to remove small amounts of any by-product.

The filtered solution can be used directly to make compounds such as hypoglycemic agents or herbicides. Alternatively, the product can be isolated by evaporation of the solvent and the hydrocarbyl isocyanate, leaving the high boiling arylsulfonyl isocyanate as a residue. Generally, these arylsulfonyl isocyanates can be distilled at reduced pressure or used without further purification.

The following examples are provided to more fully illustrate the invention but are not to be construed as limiting the scope thereof.

EXAMPLE 1

A series of runs were made to demonstrate the beneficial effect of the tertiary amine base on the rate of the phosgenation reaction claimed herein.

To a flask fitted with a water condenser, 19.2 g of o-chlorobenzenesulfonamide in 100 ml solvent was heated to reflux and any moisture present was eliminated by decantation. A dry-ice condenser was then placed on top of the water-cooled reflux condenser. The tertiary amine base and 2.0 g butyl isocyanate were then added, and the reaction mixture was refluxed for 15 minutes. Phosgene was then admitted into the vapor space of the flask at such a rate that the temperature of the reaction mass was maintained about 5°–8° C. below the boiling point of the solvent. As phosgene refluxed from the dry-ice condenser, HCl escaped the dry-ice condenser and was absorbed in water and titrated with 1 N NaOH. The rate at which HCl was formed was then plotted vs. time and is indicated in the attached FIGURE for the various tertiary amine bases used as catalyst.

| Run No. | Solvent | Phosgenation Temperature °C. |
|---------|---------|------------------------------|
| 1 | Xylenes | 133–135 |
| 2 | " | " |
| 3 | " | " |
| 4 | " | " |
| 5 | " | " |
| 6 | " | " |
| 7 | Toluene | 103–105 |
| 8 | o-dichlorobenzene | 173–175 |

| Run No. | Tertiary Base | Amount of Base (g) |
|---------|---------------|--------------------|
| 1 | None | — |
| 2 | 1,4-Diazabicyclo[2,2,2]octane | 0.10 |
| 3 | 4-Dimethylaminopyridine | 0.20 |
| 4 | N,N—Dimethylaniline | 0.21 |
| 5 | Triethylamine | 0.20 |
| 6 | Pyridine | 0.42 |
| 7 | Triethylamine | 0.20 |
| 8 | Triethylamine | 0.20 |

EXAMPLE 2

A suspension of 452 g of 2,5-dichlorobenzene sulfonamide, 260 g of cyclohexylisocyanate and 10.0 g of "Dabco" (1,4-diazabicyclo[2,2,2]octane) in 2000 ml chlorobenzene was heated for one hour to reflux in a flask fitted with a water condenser and dry-ice condenser in series, a stirrer and a thermometer. Phosgene was then added into the vapor space of the flask at such a rate that the temperature of the reaction mass was maintained at 123°–125° C. due to refluxing phosgene. During 3 hours of operation a total of 260 g of phosgene was added. The dry-ice condenser was then removed and the reaction mass refluxed to drive off excess phosgene until the temperature reached 134° C. After cooling to room temperature and filtration, the solvent and cyclohexylisocyanate were recovered by distillation at 100 mm pressure. The resulting residue was then distilled at lower pressure. Obtained were 378 g (75% yield) of 2,5-dichlorobenzenesulfonylisocyanate (B.P. 105° C./0.35 mm).

The improved yields obtained using the process claimed herein can be seen by comparing the yield obtained in the above example (75%) with the 32% yield reported for the preparation of 2,5-dichlorobenzenesulfonylisocyanate in the absence of a tertiary amine base. (U.S. Pat. No. 3,484,466 and *J. Org. Chem.* 31, 2660 (1966).

EXAMPLE 3

In a flask fitted with a water condenser and dry-ice condenser in series, a stirrer and a thermometer, a suspension of 191.6 g of o-chlorobenzenesulfonamide in 500 ml xylene was dried by azeotropically removing any moisture present. Next, 2.0 g of triethylamine and 20 g of butyl isocyanate were added, and the reaction mixture was refluxed for 15 minutes. Phosgene (105 g) was then introduced over 2.5 hours at such a rate that a temperature of 133°-135° C. was maintained. The dry-ice condenser was then removed and the reaction mass was refluxed until a temperature of 142° C. was obtained. After cooling to room temperature and filtration, the solvent and butyl isocyanate were removed under vacuum and the residue was distilled. Obtained were 196 g (90.0% yield) of o-chlorobenzenesulfonyl isocyanate (B.P. 96° C./0.5 mm).

EXAMPLE 4

A 12-liter flask, fitted with a water condenser and dry-ice condenser in series, a mechanical stirrer and a thermometer, was charged with 7 liters of xylenes and 1225 g of o-nitrobenzenesulfonamide. The slurry was heated and dried by azeotropically removing any moisture present. After cooling to 120° C., 250 g of butyl isocyanate and 4.0 g "Dabco" were added and the reaction mixture was refluxed for 45 minutes. 636 g of phosgene were then introduced over a period of 10 hours at such a rate that the temperature of the reaction mass was maintained at 130°-135° C. The dry-ice condenser was then removed and the reaction mass was refluxed to eliminate excess phosgene. After cooling to room temperature and filtration of a few solids, analysis of the filtrate showed the presence of 14.03 Wt.% o-nitrobenzenesulfonyl isocyanate (75% yield from the sulfonamide). The xylene solution of the isocyanate was then used directly for further reaction to produce an herbicidal sulfonylurea.

What is claimed is:

1. A process for preparing a 2-substituted aryl-1-sulfonyl isocyanate where the 2-substituent is an electron-withdrawing group in which an appropriately substituted arylsulfonamide is phosgenated in the presence of a catalytic quantity of a hydrocarbyl isocyanate, wherein the improvement comprises conducting the reaction in the presence of a catalytic quantity of a tertiary amine base.

2. The process of claim 1 in which the arylsulfonyl isocyanate and the arylsulfonamide are substituted at the 2-position with a group selected from Cl, F, Br, $NO_2$, $CF_3$ ($C_1$-$C_4$alkyl)$SO_2$— and ($C_1$-$C_2$alkyl)$_2$-$NSO_2$—.

3. The process of claim 1 in which the arylsulfonyl isocyanate and the arylsulfonamide are, respectively, a benzenesulfonyl isocyanate and a benzenesulfonamide.

4. The process of claim 2 in which the arylsulfonyl isocyanate and the arylsulfonamide are, respectively, a benzenesulfonyl isocyanate and a benzenesulfonamide.

5. The process of claim 4 in which a benzenesulfonyl isocyanate of the formula

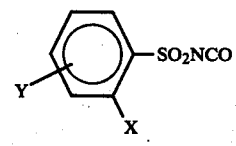

wherein
X is Cl, F, Br, $CF_3$, ($C_1$-$C_4$alkyl)$SO_2$—, ($C_1$-$C_2$alkyl)$NSO_2$—, or $NO_2$; and
Y is H, Cl, Br, $CH_3$ or $OCH_3$;
is prepared by phosgenation of the appropriate benzenesulfonamide.

6. The process of claim 5 wherein X is Cl, F, Br, $CF_3$, ($C_1$-$C_4$alkyl)$SO_2$—, ($C_1$-$C_2$alkyl)$_2$NSO_2$— or $NO_2$.

7. The process of claim 5 in which the benzenesulfonyl isocyanate is o-chlorobenzenesulfonyl isocyanate.

8. The process of claim 5 in which the benzenesulfonyl isocyanate is o-nitrobenzenesulfonyl isocyanate.

9. The process of claim 5 in which the benzenesulfonyl isocyanate is 2,5-dichlorobenzenesulfonyl isocyanate.

10. The process of any of claims 1-4, 5, and 7-9 wherein the tertiary amine base is selected from the group consisting of pyridine, triethylamine, 1,4-diazabicyclo[2,2,2]octane, 4-dimethylaminopyridine, N,N-dimethylaniline, trimethylamine, N,N-diethylaniline, N-methylpiperidine, and N,N'-dimethylpiperazine.

11. The process of claim 10 wherein the tertiary amine base is 1,4-diazabicyclo[2,2,2]octane.

12. The process of claim 10 wherein the tertiary amine base is triethylamine.

13. The process of any of claims 1-4, 5, and 7-12 wherein the hydrocarbyl isocyanate is selected from the group consisting of $C_4$-$C_{10}$ alkyl isocyanates and $C_5$-$C_8$ cycloalkyl isocyanates.

14. The process of any of claims 1-4, 5, and 7-12 wherein the tertiary amine base is present in an amount of about 0.2 to 5.0 grams per mole of arylsulfonamide.

* * * * *